(12) United States Patent
Lin et al.

(10) Patent No.: US 10,159,511 B2
(45) Date of Patent: Dec. 25, 2018

(54) ADJUSTABLE EXTERNAL FIXATOR (71) Applicant: E-DA HEALTHCARE GROUP, Kaohsiung (TW)

(72) Inventors: Ting-Sheng Lin, Kaohsiung (TW); Ching-Hou Ma, Kaohsiung (TW); Jiun-Ru Jiang, Kaohsiung (TW)

(73) Assignee: E-DA HEALTHCARE GROUP, Kaohsiung (TW)

( * ) Notice: Subject to any disclaimer, the term of this patent is extended or adjusted under 35 U.S.C. 154(b) by 156 days.

(21) Appl. No.: 15/336,464

(22) Filed: Oct. 27, 2016

(65) Prior Publication Data
US 2017/0281235 A1 Oct. 5, 2017

(30) Foreign Application Priority Data

Apr. 1, 2016 (TW) .............................. 105110616 A (51) Int. Cl.
| A61B 17/66 | (2006.01) |
| A61B 17/64 | (2006.01) |
| A61B 17/62 | (2006.01) |
| A61B 17/88 | (2006.01) |
| A61B 17/60 | (2006.01) |
| A61B 17/90 | (2006.01) |

(52) U.S. Cl.
CPC ............ *A61B 17/645* (2013.01); *A61B 17/62* (2013.01); *A61B 17/6475* (2013.01); *A61B 17/66* (2013.01); *A61B 17/8858* (2013.01); *A61B 17/8872* (2013.01); *A61B 2017/603* (2013.01); *A61B 2017/90* (2013.01)

(58) Field of Classification Search
CPC ..... A61B 17/60; A61B 17/64; A61B 17/6466; A61B 17/6475; A61B 17/66; A61B 17/663; A61B 17/666; A61B 17/7014; A61B 17/7216; A61B 17/7225; A61B 17/8004; A61B 17/8009; A61B 17/8023
See application file for complete search history.

(56) References Cited

U.S. PATENT DOCUMENTS

| 4,548,199 | A | * | 10/1985 | Agee .................. A61B 17/1782 606/55 |
| 4,573,459 | A | * | 3/1986 | Litton .................... A61B 17/66 606/58 |
| 4,730,608 | A | * | 3/1988 | Schlein .................. A61B 17/66 606/57 |
| 5,364,396 | A | * | 11/1994 | Robinson ............. A61B 17/663 606/105 |
| 6,024,745 | A | * | 2/2000 | Faccioli ................. A61B 17/66 606/54 |
| 6,171,307 | B1 | * | 1/2001 | Orlich ................... A61B 17/66 606/53 |

(Continued)

FOREIGN PATENT DOCUMENTS

WO   WO 2017134486 A1 * 8/2017 ......... A61B 17/6466

*Primary Examiner* — Lynnsy Summitt
(74) *Attorney, Agent, or Firm* — WPAT, PC (57) ABSTRACT

The present disclosure provides an adjustable external fixator which can be utilized in bone transport or bone lengthening. The adjustable external fixator includes a body, a positioning member, a bone coupling member, and a threaded rod. The body includes a slideway. At least one of the positioning member and the bone coupling member is slidably coupled to the slideway of the body.

6 Claims, 9 Drawing Sheets

(56) References Cited

U.S. PATENT DOCUMENTS

| | | | | |
|---|---|---|---|---|
| 7,252,668 | B2* | 8/2007 | Wolgen | A61B 17/663 606/53 |
| 8,182,483 | B2* | 5/2012 | Bagnasco | A61B 17/6483 606/58 |
| 8,894,649 | B2* | 11/2014 | Lee, Jr. | A61B 17/6466 606/59 |
| 2003/0144669 | A1* | 7/2003 | Robinson | A61B 17/66 606/90 |
| 2006/0058798 | A1* | 3/2006 | Roman | A61B 17/8004 606/71 |
| 2007/0123858 | A1* | 5/2007 | Strub | A61B 17/66 606/54 |
| 2007/0162045 | A1* | 7/2007 | Ahmad | A61B 17/663 606/105 |
| 2011/0125162 | A1* | 5/2011 | Noon | A61B 17/663 606/105 |
| 2011/0172664 | A1* | 7/2011 | Bagnasco | A61B 17/6483 606/59 |
| 2012/0150180 | A1* | 6/2012 | Verma | A61B 17/6416 606/59 |
| 2012/0239035 | A1* | 9/2012 | Li | A61B 17/663 606/57 |

* cited by examiner

ADJUSTABLE EXTERNAL FIXATOR

CROSS REFERENCE TO RELATED APPLICATIONS

The application claims the benefit of Taiwan application serial No. 105110616, filed on Apr. 1, 2016, and the subject matter of which is incorporated herein by reference.

BACKGROUND OF THE INVENTION

1. Field of the Invention

The present invention generally relates to an adjustable external fixator and, more particularly, to an adjustable external fixator utilized in bone lengthening or bone transport.

2. Description of the Related Art

Concerning the treatment of a patient with open bone fracture, after the fracture site is treated and cleaned, some of the bone and soft tissue at the fracture site may be found seriously broken. Hence, the surgeon may attach a conventional adjustable external fixator 9 around the fracture site, such that the bone and soft tissue at the fracture site can steadily regenerate.

Figure 1:
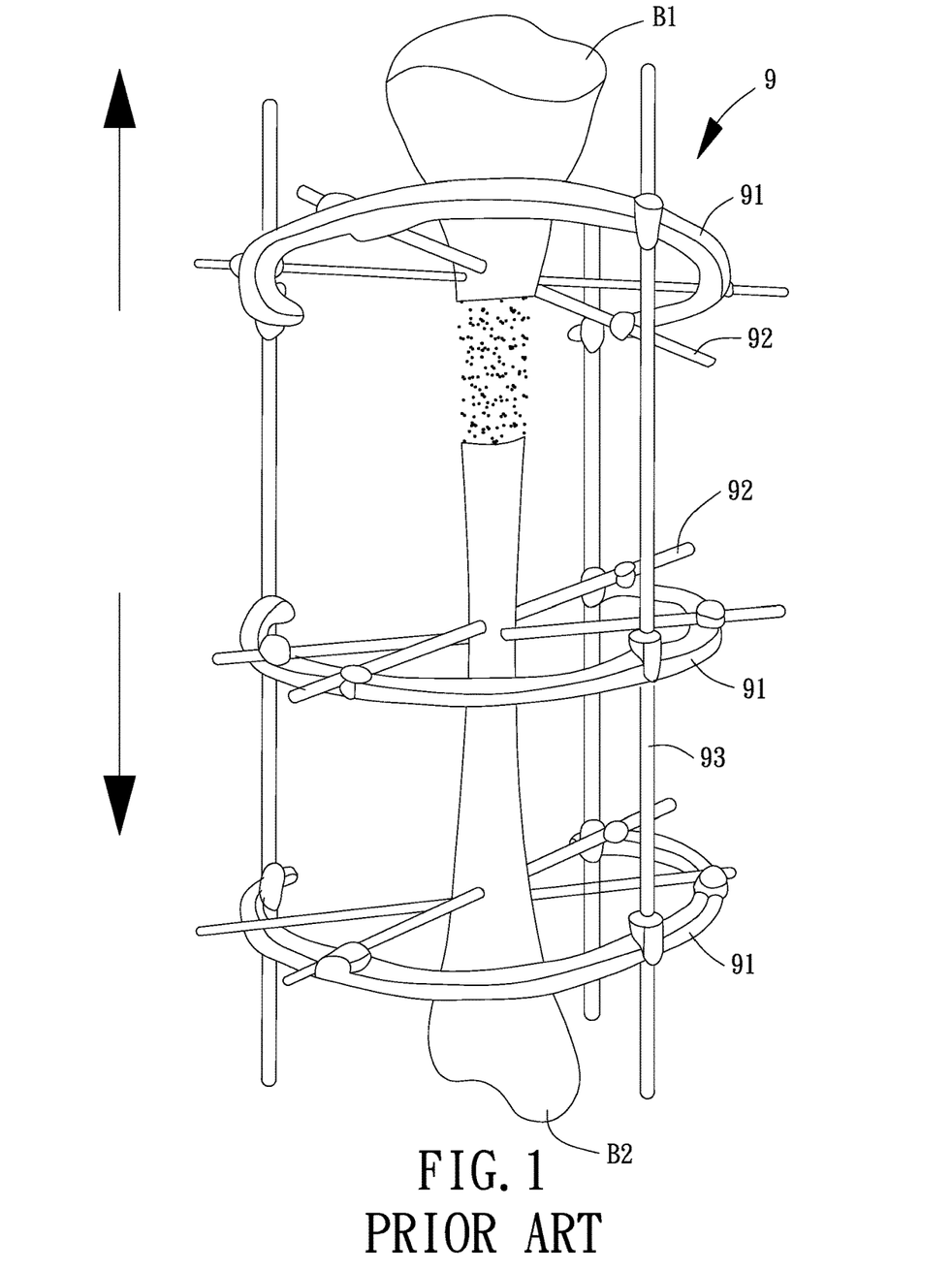
FIG. 1 is a perspective view of a conventional adjustable external fixator, which shows the conventional adjustable external fixator in use.

With references to FIG. 1, the conventional adjustable external fixator 9 includes a plurality of rings 91, with each ring 91 fixed around the bone sections on the opposite sides of the fracture site (hereinafter referred as "bone section B1" and "bone section B2") via a plurality of pins 92. Two adjacent rings 91 are connected to each other via a plurality of rods 93. The length of each rod 93 is adjustable, such that a distance between two adjacent rings 91 can be varied.

The surgeon can lengthen the distance between the two adjacent rings 91 by adjusting the length of the rods 93. Accordingly, the distance between the bone section B1 and the bone section B2 can be increased, thus the bone and soft tissue can gradually regenerate between these two bone sections B1 and B2.

However, the conventional adjustable external fixator 9 is fixed around the two bone sections B1 and B2, and the rings 91 cannot directly adhere to the limb of the patient. Besides, the conventional external fixator 9 has lots of complicated components, resulting in large volume and heavy weight which cause extra burden to daily living of the patient.

SUMMARY OF THE INVENTION

It is therefore the objective of this invention to provide an adjustable external fixator with smaller volume and lighter weight than the conventional adjustable external fixator described above, thus reducing the burden to the patient's daily living.

The adjustable external fixator includes a body, a positioning member, a bone coupling member, and a threaded rod. The body has opposite first and second ends and a first direction extending from the first end toward the second end. The body includes a fixation portion adjacent to the first end and away from the second end. The body further includes a slideway extending in the first direction from the fixation portion. The positioning member is arranged at the body. The positioning member includes a screw hole penetrating through the positioning member in the first direction. The bone coupling member is arranged at the slideway of the body. The bone coupling member includes at least one bone coupling hole having an extending direction not parallel to the first direction, and the positioning member is located between the fixation portion of the body and the bone coupling member. The threaded rod includes a threaded section fastened with the screw hole of the positioning member. An end of the threaded rod is adapted to abut against the bone coupling member, and at least one of the positioning member and the bone coupling member is slidably coupled to the slideway of the body.

Since the adjustable external fixator of the present disclosure has the body that can adhered on the patient's limb as well as the positioning member and the bone coupling member coupled with the body, the adjustable external fixator is provided with smaller volume and lighter weight, thus reducing the burden to the daily living of the patient.

In a form shown, the threaded rod further includes a head and a terminal section. The threaded section is located between the head and the terminal section. The bone coupling member includes a blind hole aligned with the screw hole of the positioning member and adapted for receiving the terminal section of the threaded rod. The bone coupling member further includes a through hole communicating with the blind hole. The through hole has an extending direction not parallel to an extending direction of the blind hole. A circular groove is arranged at the terminal section of the threaded rod. The circular groove communicates with the through hole when the terminal section of the threaded rod is received in the blind hole, and the through hole is adapted for a securing component to extend therethrough into the circular groove. As such, the surgeon can fix the position of the threaded rod using the securing component to prevent disengagement of the threaded rod, thus improving engagement stability between the threaded rod and the bone coupling member.

In the form shown, the positioning member is integrally formed at the body. As such, it is not needed for the surgeon to adjust the distance between the positioning member and the body, thus improving convenience of the surgery.

In the form shown, the positioning member includes at least one bone coupling hole having an extending direction not parallel to the first direction. As such, the surgeon can stably position the positioning member on the patient's bone using the at least one second pin.

In the form shown, the slideway is in a form of two elongated rods. The bone coupling member includes two apertures extending in the first direction through two opposite sides of the bone coupling member. Each of the two apertures includes a through groove to form an adjustable slit, and the two elongated rods of the body respectively extend in the two apertures. As such, the surgeon can adjust the engagement level between the two apertures and the slideway by varying the width of the through grooves. Hence, the adjustable external fixator can be utilized in bone transport and bone lengthening.

In the form shown, the slideway is in a form of two elongated rods. The positioning member includes two apertures extending in the first direction through two opposite sides of the positioning member. Each of the two apertures includes a through groove to form an adjustable slit, and the two elongated rods of the body respectively extend in the two apertures.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

In the various figures of the drawings, the same numerals designate the same or similar parts. Furthermore, when the terms "first", "second", "third", "fourth", "inner", "outer", "top", "bottom", "front", "rear" and similar terms are used hereinafter, it should be understood that these terms have reference only to the structure shown in the drawings as it would appear to a person viewing the drawings, and are utilized only to facilitate describing the invention.

DETAILED DESCRIPTION OF THE INVENTION

Figure 6:
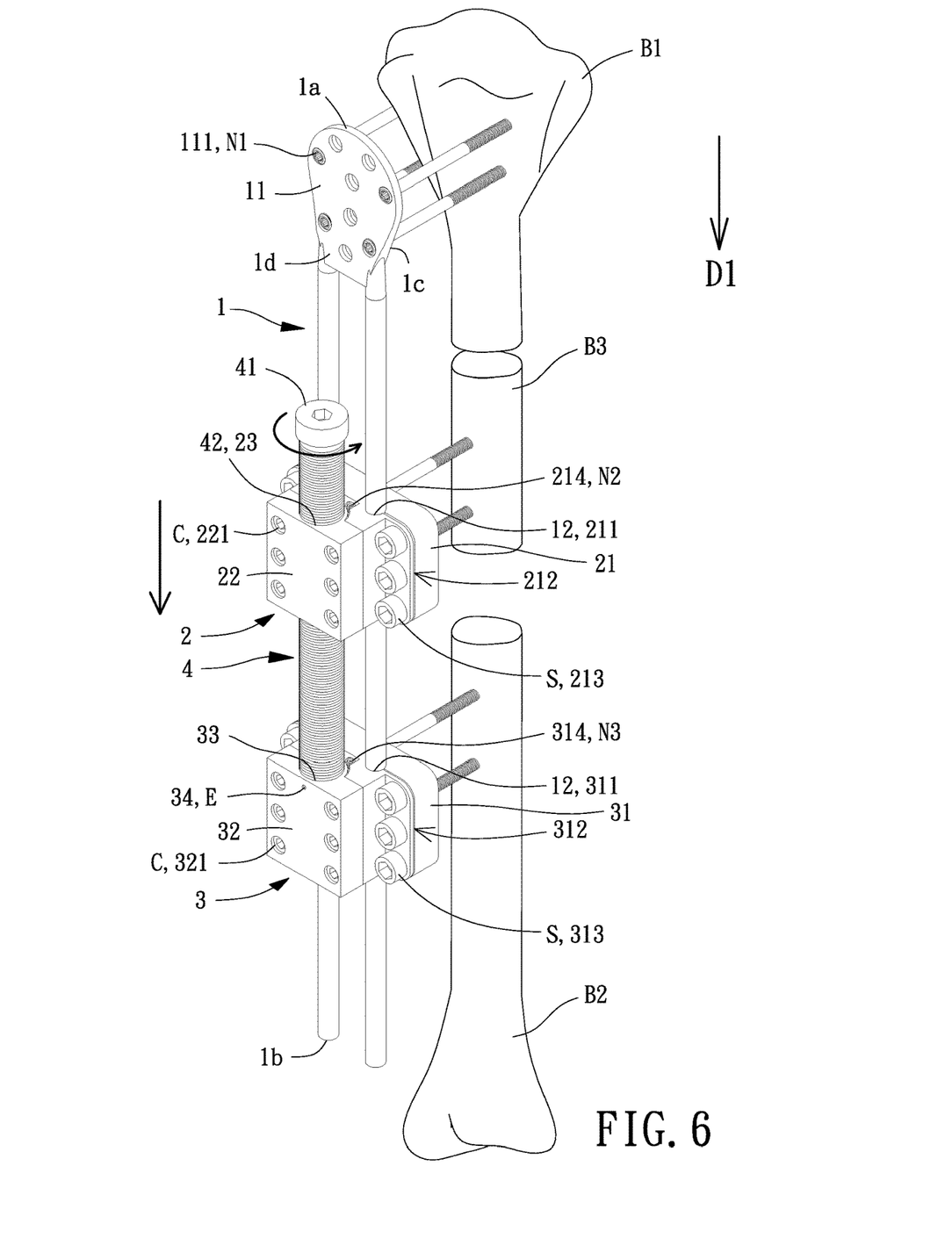
FIG. 6 is a perspective view of the adjustable external fixator according to the first embodiment of the present disclosure when utilized in bone transport.

The term "bone transport" used hereinafter in the present disclosure is widely used for treating the patient having bone and soft tissue seriously broken in a wide range. The surgeon may fix the position of two opposite sides of the fracture (as shown in FIG. 6, hereinafter referred as "bone section B1" and "bone section B2"), and use an end of the bone section B1 extending toward the bone section B2 (hereinafter referred as "bone section B3") as a bridge between the two bone sections B1 and B2. By slowly moving the bone section B3 from the bone section B1 to the bone section B2, the bone and soft tissue between the bone sections B1 and B3 as well as the bone and soft tissue between the bone sections B3 and B2 can be steadily regenerate.

Figure 2:
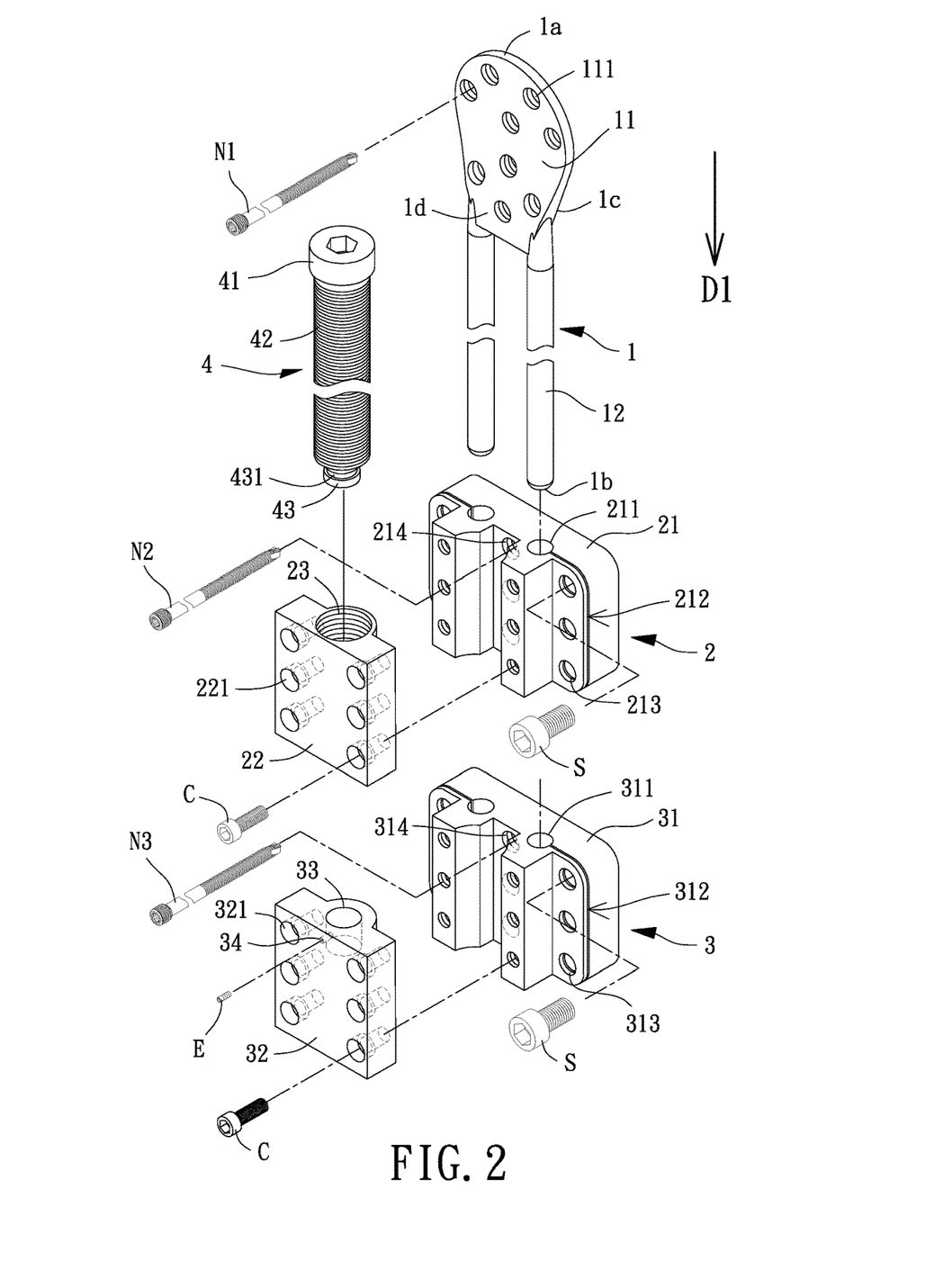
FIG. 2 is a perspective, exploded view of an adjustable external fixator according to a first embodiment of the present disclosure.
Figure 3:
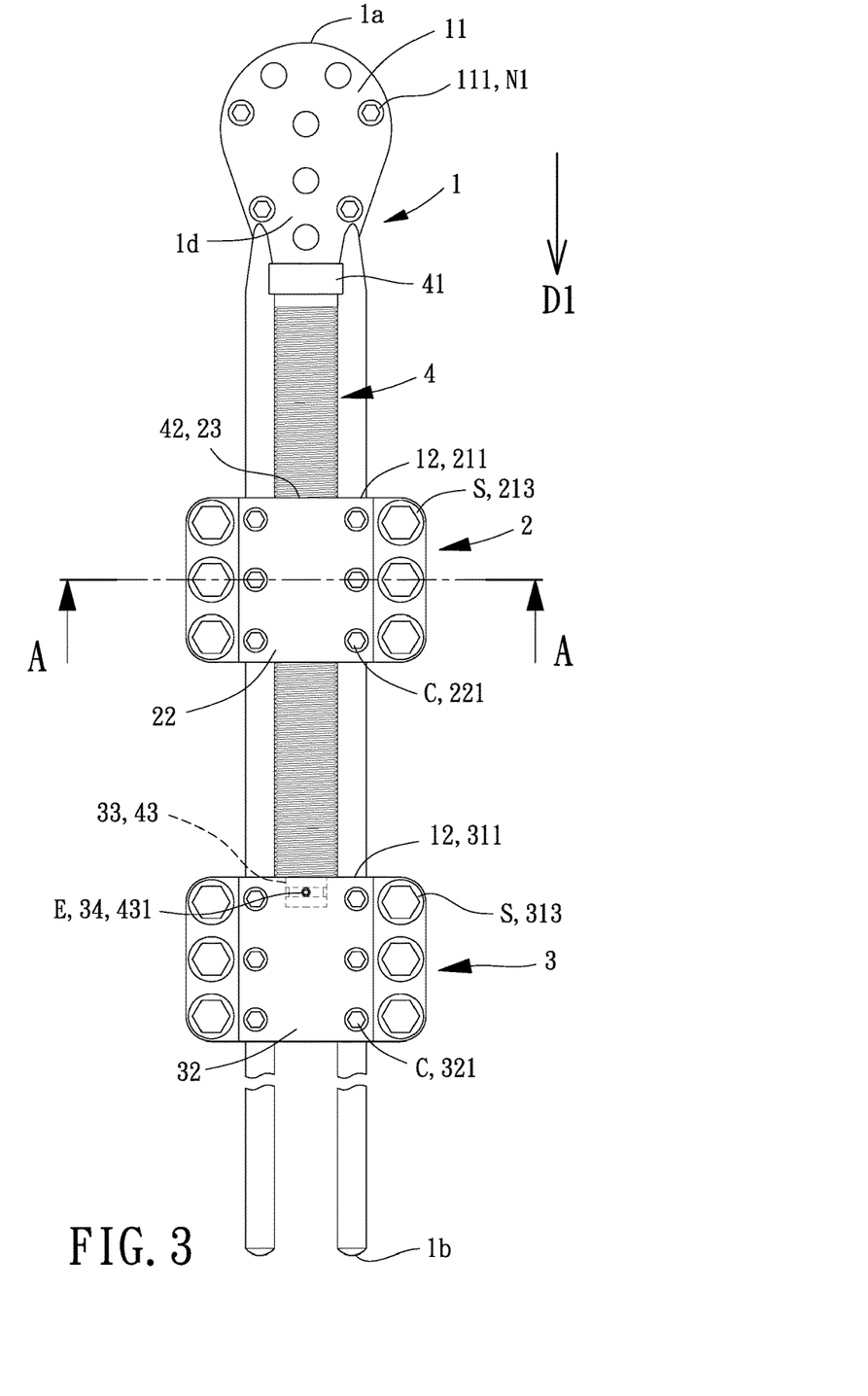
FIG. 3 is a front view of the adjustable external fixator according to the first embodiment of the present disclosure when components of the adjustable external fixator are coupled together.
Figure 4:
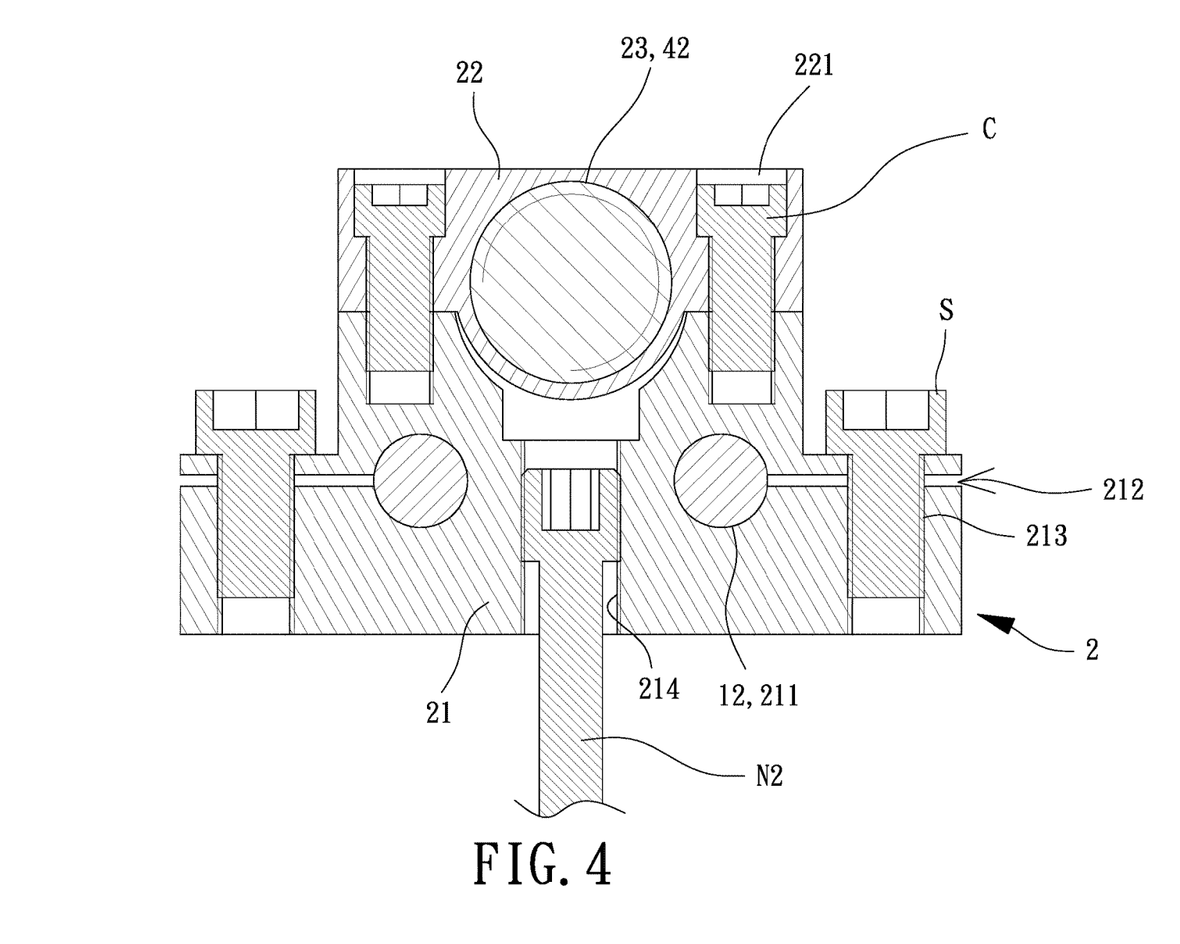
FIG. 4 is a cross sectional view along the A-A line of FIG. 3 of the adjustable external fixator according to the first embodiment of the present disclosure.

With references to FIGS. 2-4, an adjustable external fixator according to a first embodiment of the present disclosure includes a body 1, a positioning member 2, a bone coupling member 3 and a threaded rod 4.

Specifically, the body 1 has opposite first and second ends 1a and 1b. The body 1 is preferably arranged parallel to the extending direction of the patient's long bone, such that the bone and soft tissue of the patient can grow in the extending direction of the long bone. For facilitating description of the present disclosure, the body 1 is longitudinally extends from the first end 1a to the second end 1b in a first direction D1.

The body 1 further has a coupling side 1c and an adjusting side 1d opposite to the coupling side 1c, with the coupling side 1c and the adjusting side 1d located between the first and second ends 1a and 1b. When the adjustable external fixator is in use, the coupling side 1c of the body 1 can face the limb of the patient.

The body 1 includes a fixation portion 11 adjacent to the first end 1a and away from the second end 1b. The fixation portion 11 includes a plurality of bone positioning holes 111 extending through the coupling side 1c and the adjusting side 1d of the body 1. Each bone positioning hole 111 is adapted for a first pin N1 to extend through, such that the body 1 can be fixed to the patient's bone (such as the bone section B1 shown in FIG. 6) via the pins N1. The plurality of bone positioning holes 111 can be threaded, such that the pins N1 can be fastened with the bone positioning holes 111. Preferably, the fixation portion 11 can be made of a flexible material for closely adhering to the patient's limb, assuring that the fixation portion 11 can be securely positioned. The body 1 can further include a slideway 12 extending in the first direction D1 from the fixation portion 11. In the first embodiment, the slideway 12 can be in the form of two elongated rods, but is not limited thereto.

With references to FIGS. 2-4, the positioning member 2 can be coupled to the slide way 12. The positioning member 2 can be a single component which is integrally formed. Or, the positioning member 2 can include a first positioning member 21 and a second positioning 22 as shown in the first embodiment, with the first and second positioning members 21 and 22 able to be coupled with each other via a plurality of coupling components C.

The first positioning member 21 can have two apertures 211 extending in the first direction D1 through two opposite sides of the first coupling portion 21. Each aperture 211 has a through groove 212 communicating therewith to form an adjusting slit, thus the size of the aperture 211 can be adjusted by varying the width of the through groove 212. The two apertures 211 are adapted for the slideway 12 of the body to extend therethrough, such that the first positioning member 21 is able to slide along the slideway 12 in the first direction D1. Accordingly, the surgeon can enlarge the width of the through groove 212 to correspondingly enlarge the size of the aperture 211, making the first positioning member 21 able to slide smoothly along the slideway 12. Alternatively, the surgeon can reduces the width of the through groove 212 to make the aperture 211 tightly engaged with the slideway 12, such that the first positioning member 21 cannot slide along the slideway 12. That is, the surgeon can adjust the engagement level between the two apertures 211 and the slideway 12 by varying the width of the through grooves 212.

For instance, width adjustment of each through groove 212 can be achieved by a plurality of threaded holes 213 arranged at the first positioning member 21 and extending through the through groove 212. A plurality of screw components S is fastened with the plurality of threaded holes 213 for varying the width of the through groove 212. Hence, when the apertures 211 and the slideway 12 are tightly engaged with each other, the first positioning member 21 is thus securely coupled with the body 1 and cannot slide along the slideway 12. Alternatively, when the engagement between the apertures 211 and the slideway 12 becomes loose, the first positioning member 21 is able to slide along the slideway 12.

The first positioning member 21 may further include at least one bone coupling hole 214, with an extending direction of the at least one bone coupling hole 214 not parallel to the first direction D1. The at least one bone coupling hole 214 is adapted for at least one second pin N2 to extend therethrough, such that the positioning member 2 can be securely fixed to the patient's bone (e.g. the bone section B3 shown in FIG. 6) via the at least one second pin N2.

The second positioning member 22 can be integrally formed with the first positioning member 21. Alternatively, as shown in the figures, the second positioning member 22 can be coupled with the first positioning member 21 via the plurality of coupling components C extending in a plurality of positioning holes 221. The second positioning member 22 includes a screw hole 23 penetrating through the second positioning member 22 in the first direction D1. The screw hole 23 can be fastened with the threaded rod 4.

The bone coupling member 3 can have a structure similar to that of the positioning member 2. That is, the bone coupling member 3 can be a single component which is integrally formed. Alternatively, in the first embodiment of the present disclosure, the bone coupling member 3 includes a first bone coupling member 31 and a second bone coupling member 32 coupled with the first bone coupling member 31 via a plurality of coupling components C extending through a plurality of positioning holes 321. The first bone coupling member 31 can include two apertures 311 holding the slideway 12 of the body 1, and the positioning member 2 can be located between the fixation portion 11 of the body 1 and the bone coupling member 3. Similar to the two apertures 211 of the first positioning member 21, each aperture 311 of the first bone coupling member 31 can include a through groove 312. Besides, the first bone coupling member 31 can further include a plurality of threaded holes 313 extending through the through groove 312 and adapted for a plurality of screw components S to be fastened with, such that the width of the through groove 312 can be adjusted. Accordingly, the surgeon can enlarge the width of the through groove 312 to correspondingly enlarge the size of the aperture 311, making the first bone coupling member 31 able to slide smoothly along the slideway 12. Alternatively, the surgeon can reduces the width of the through groove 312 to make the aperture 311 tightly engaged with the slideway 12, such that the first bone coupling member 31 cannot slide along the slideway 12.

In addition, the first bone coupling member 31 can also include at least one bone coupling hole 314 extending in a direction not parallel to the first direction. Hence, by utilizing at least one third pin N3 extending in the at least one bone coupling hole 314, the first bone coupling member 31 can be securely fixed to the patient's bone (such as the bone section B2 shown in FIG. 6).

The threaded rod 4 can be substantially arranged parallel to the first direction D1, and can be located at the adjusting side 1d of the body 1. The threaded rod 4 has a head 41, a threaded section 42 and a terminal section 43, with the threaded section 42 located between the head 41 and the terminal section 43. The maximal diameter of the head 41 is larger than that of the threaded section 42, and the maximal diameter of the terminal section 43 is smaller than the minimal diameter of the threaded section 42. Accordingly, the head 41 can locate at a side of the positioning member 2, the threaded section 42 can be fastened with the screw hole 23 of the positioning member 2, and the terminal section 43 can extend to and connect with the bone coupling member 3. The threaded section 42 can be left-handed or right-handed, such that the surgeon can make the positioning member 2 or the bone coupling member 3 slide along the slideway 12 in the first direction by rotating the threaded rod 4 (described as follows).

In the present embodiment, the bone coupling member 3 can further include a blind hole 33 aligned with the screw hole 23 of the positioning member 2 for receiving the terminal section 43 of the threaded rod 4.

The bone coupling member 3 further includes a through hole 34 communicating with the blind hole 33, with the extending direction of the through hole 34 not parallel to the extending direction of the blind hole 33. The threaded rod 4 can include a circular groove 431 at the terminal section 43. When the terminal section 43 of the threaded rod 4 is received in the blind hole 33, the circular groove 431 can align with the through hole 34, such that a securing component E (e.g. a bolt) can extend through the through hole 34 into the circular groove 431. The above arrangement prevents disengagement of the terminal section 43 from the blind hole 33, enhancing engaging strength between the threaded rod 4 and the bone coupling member 3. Besides, rotation of the threaded rod 4 makes the bone coupling member 3 slide along the slideway 12.

Figure 5:
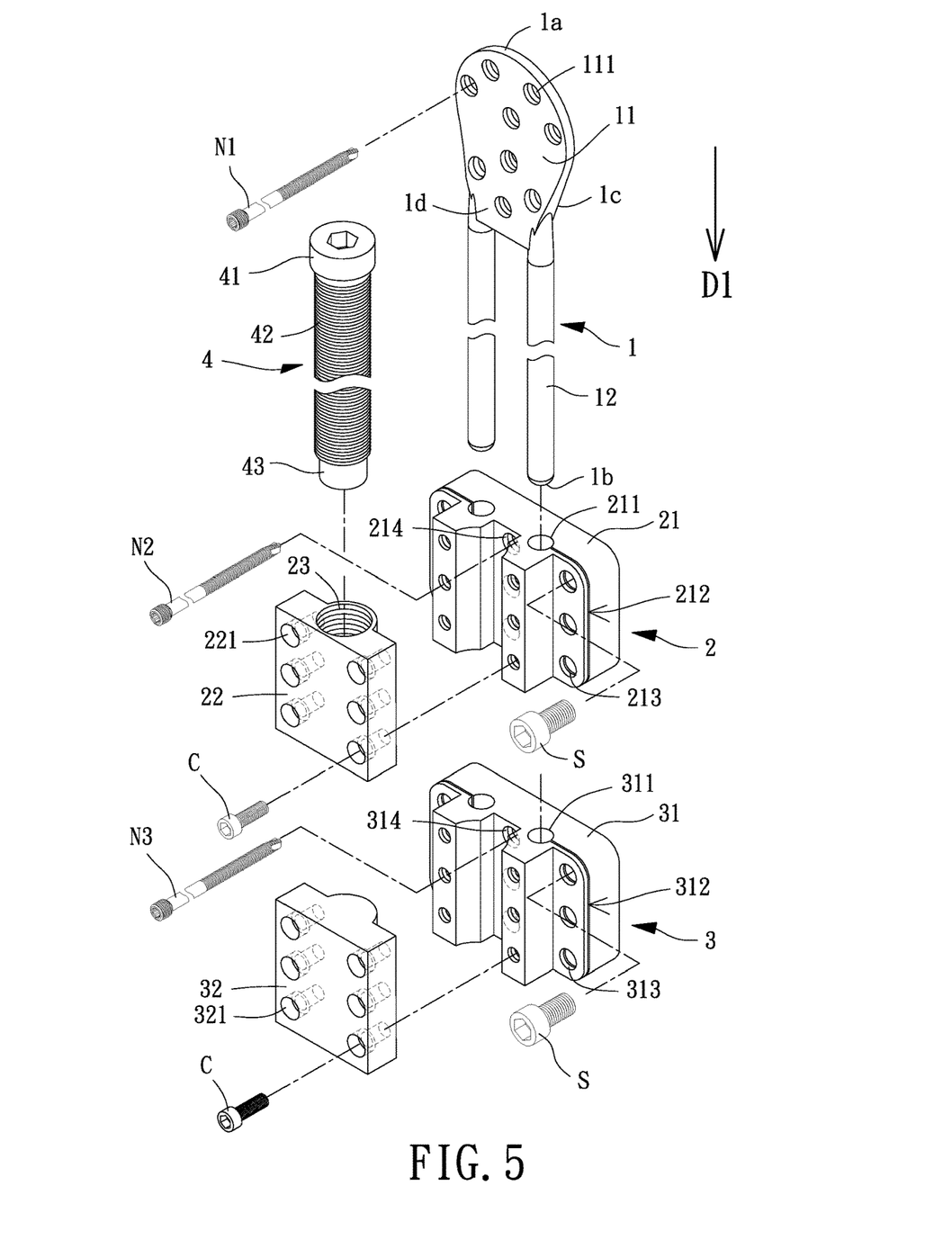
FIG. 5 is a perspective, exploded view of an adjustable external fixator according to a second embodiment of the present disclosure.

FIG. 5 shows an adjustable external fixator according to a second embodiment of the present disclosure. In this embodiment, the bone coupling member 3 does not include a blind hole 33. Hence, the threaded rod 4 can only abut against the bone coupling member 3 via the terminal section 43 (as shown in the figures, the terminal section 43 abuts against an end of the positioning portion 2). Besides, rotating the threaded rod 4 can only make the bone coupling member 3 slide along the slideway 12 in the first direction D1.

With references to FIG. 6, the adjustable external fixator of the first and second embodiments can be utilized in bone transport. The surgeon can sequentially couple the positioning member 2 and the bone coupling member 3 to the slideway 12 of the body 1, with the positioning member 2 located between the fixation portion 11 of the body 1 and the bone coupling member 3. Next, the surgeon can fix the fixation portion 11 of the body 1 to the bone section B1 via the plurality of first pins N1, fix the positioning member 2 to the bone section B3 via the at least one second pins N2, and fix the bone coupling member 3 to the bone section B2 via the at least one third pins N3. Hence, the adjustable external fixator can be attached to the fracture site of the patient.

The surgeon can then fasten the threaded section 42 of the threaded rod 4 in the screw hole 23 of the positioning member 2, and make the terminal section of 43 of the threaded rod 4 abut against the bone coupling member 3 (e.g. making the terminal section 43 extend into the blind hole 33 as shown in the figures). Accordingly, the threaded rod 4 can be arranged at the adjusting side 1d of the body 1, with a predetermined distance set between the positioning member 2 and the bone coupling member 3. And then, the surgeon can adjust the width of the through groove 212 and the width of the through groove 312, making the positioning member 2 able to slide along the slideway 12 as well as the bone coupling member 3 tightly coupled with the slideway 12 of the body 1. Thus, the assembly of the adjustable external fixator is finished.

Since the bone coupling member 3 is tightly engaged with the body 1, the surgeon can rotate the threaded rod 4 to make the positioning member 2 slide along the slideway 12 in the first direction D1. For instance, the positioning member 2 can move in the first direction for 1 mm per day, such that the bone and soft tissue of the fracture site (i.e. between the bone sections B1 and B3) can regenerate in an appropriate rate.

Figure 7:
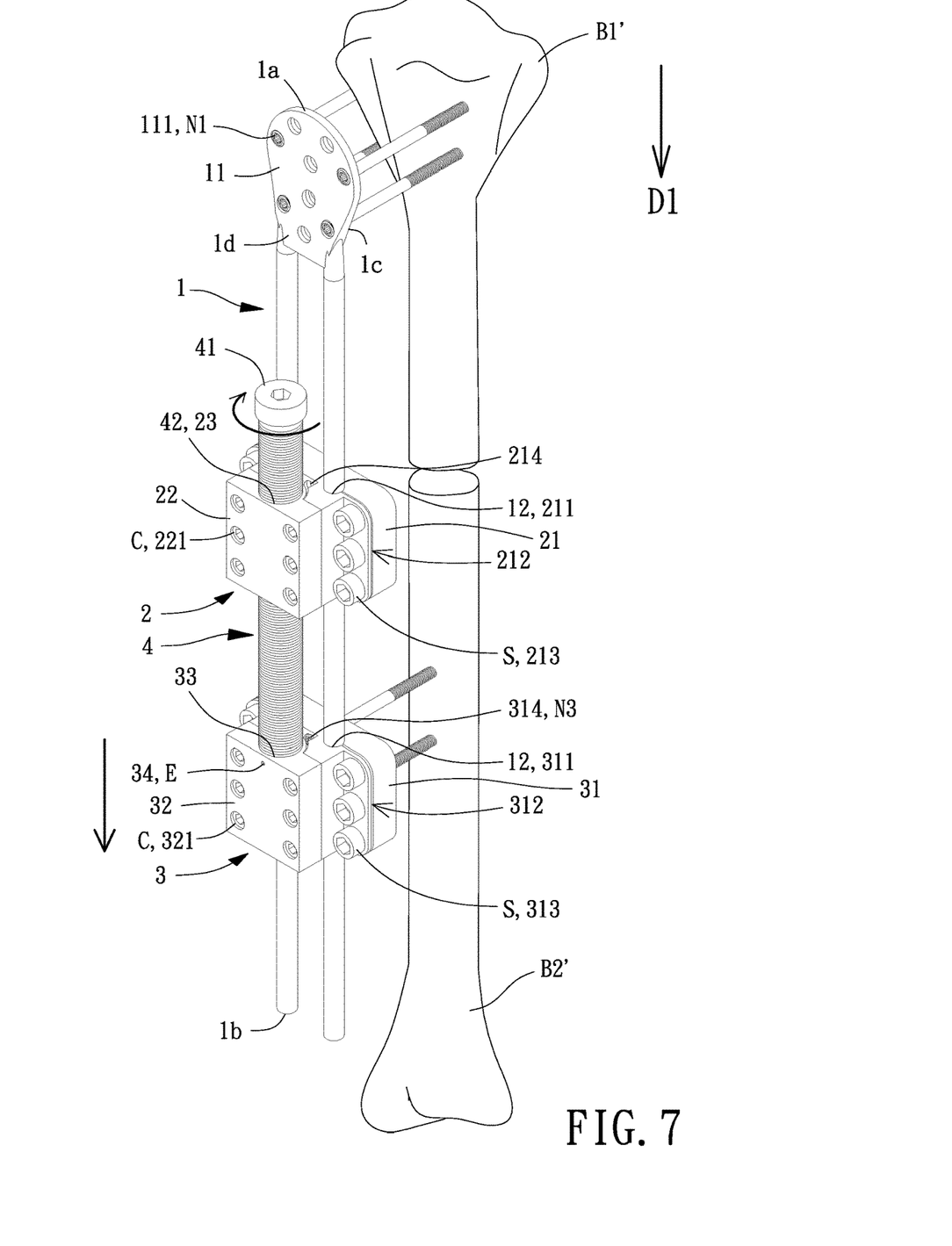
FIG. 7 is a perspective view of the adjustable external fixator according to the first embodiment of the present disclosure when utilized in bone lengthening.

With references to FIG. 7, the adjustable external fixator can be further utilized in bone lengthening, for treating patient with leg length discrepancy. The surgeon can initially perform an osteotomy to fracture the patient's long bone, forming a proximal bone section B1' near the patient's trunk and a distal bone section B2' away from the patient's trunk. By gradually moving the distal bone section B2' in a direction away from the trunk, the bone and soft tissue between the proximal bone section B1' and the distal bone section B2' can regenerate, thus lengthening the patient's long bone.

Specifically, the surgeon can assemble the adjustable external fixator in a way similar to that described above. However, it is noteworthy that the surgeon can fix the fixation portion 11 of the body 1 to the proximal bone section B1' via the plurality of first pins N1, and fix the bone coupling section 3 to the distal bone section B2' via the at least one third pins N3. Next, the surgeon can adjust the width of the through grooves 212 and 312, making that the positioning member 2 tightly engaged with the slideway 12 of the body 1 while the bone coupling member 3 is able to slide along the slideway 12. Accordingly, the adjustable external fixator can be attached to the long bone of the patient.

Since the positioning member 2 is tightly engaged with the body 1, the surgeon can rotate the threaded rod 4 to make the bone coupling member 3 move along the slideway 12 in the first direction D1. Hence, the bone and soft tissue between the proximal bone section B1' and the distal bone section B2' can regenerate, lengthening the long bone of the patient.

Figure 8:
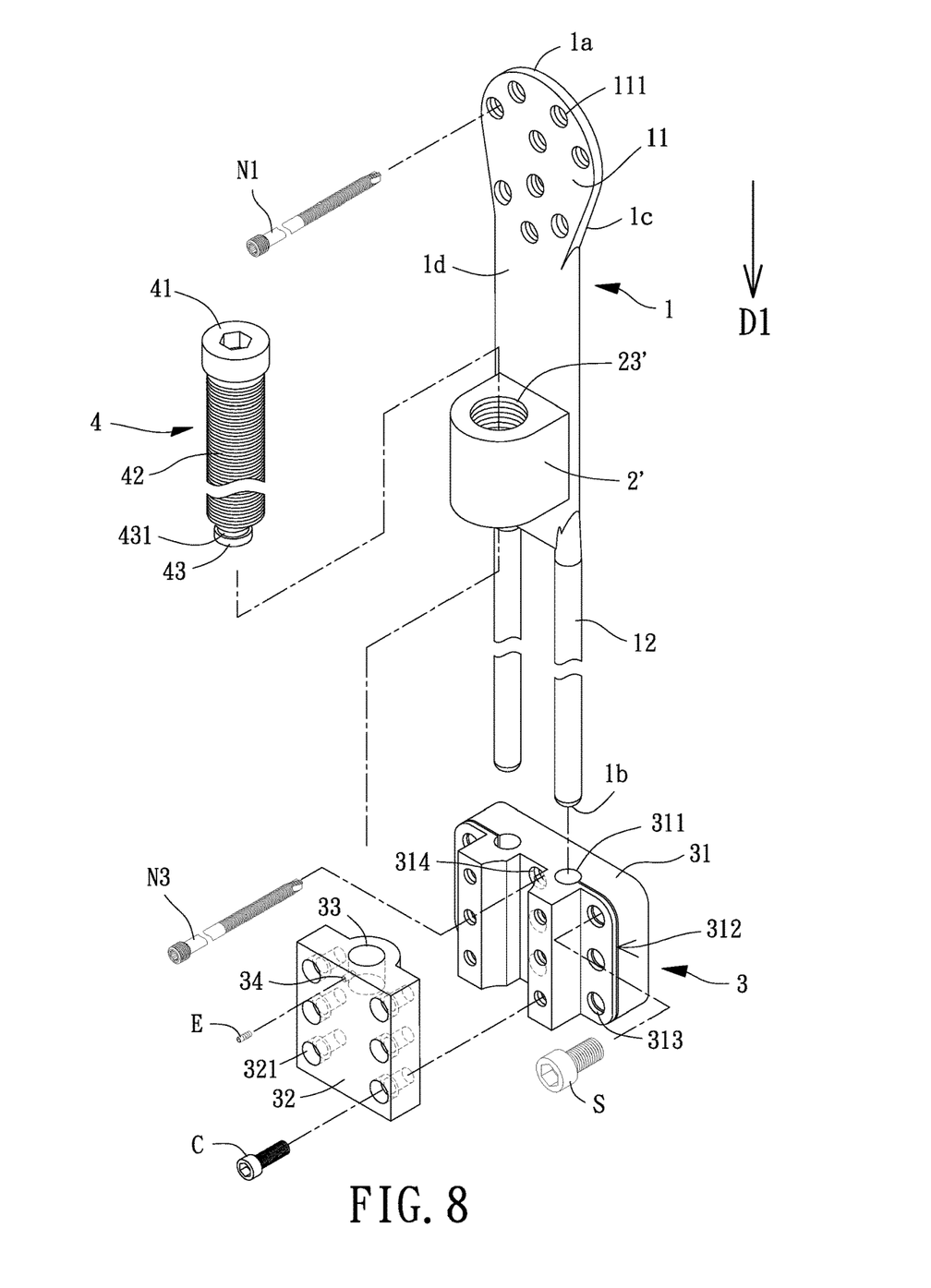
FIG. 8 is a perspective, exploded view of an adjustable external fixator according to a third embodiment of the present disclosure.

Furthermore, the positioning member 2 can be integrally formed on the body 1. For instance, as shown in FIG. 8, an adjustable external fixator according to a third embodiment of the present disclosure can include a body 1, a positioning member 2', a bone coupling member 3 and an threaded rod 4. The structure of the body 1, the bone coupling member 3 and the threaded rod 4 are the same as those described in the first and second embodiments, thus are not described again. The positioning member 2' is integrally formed on the body 1. Similarly, the positioning member 2' also includes a screw hole 23' adapted to be fastened with the threaded rod 4.

Figure 9:
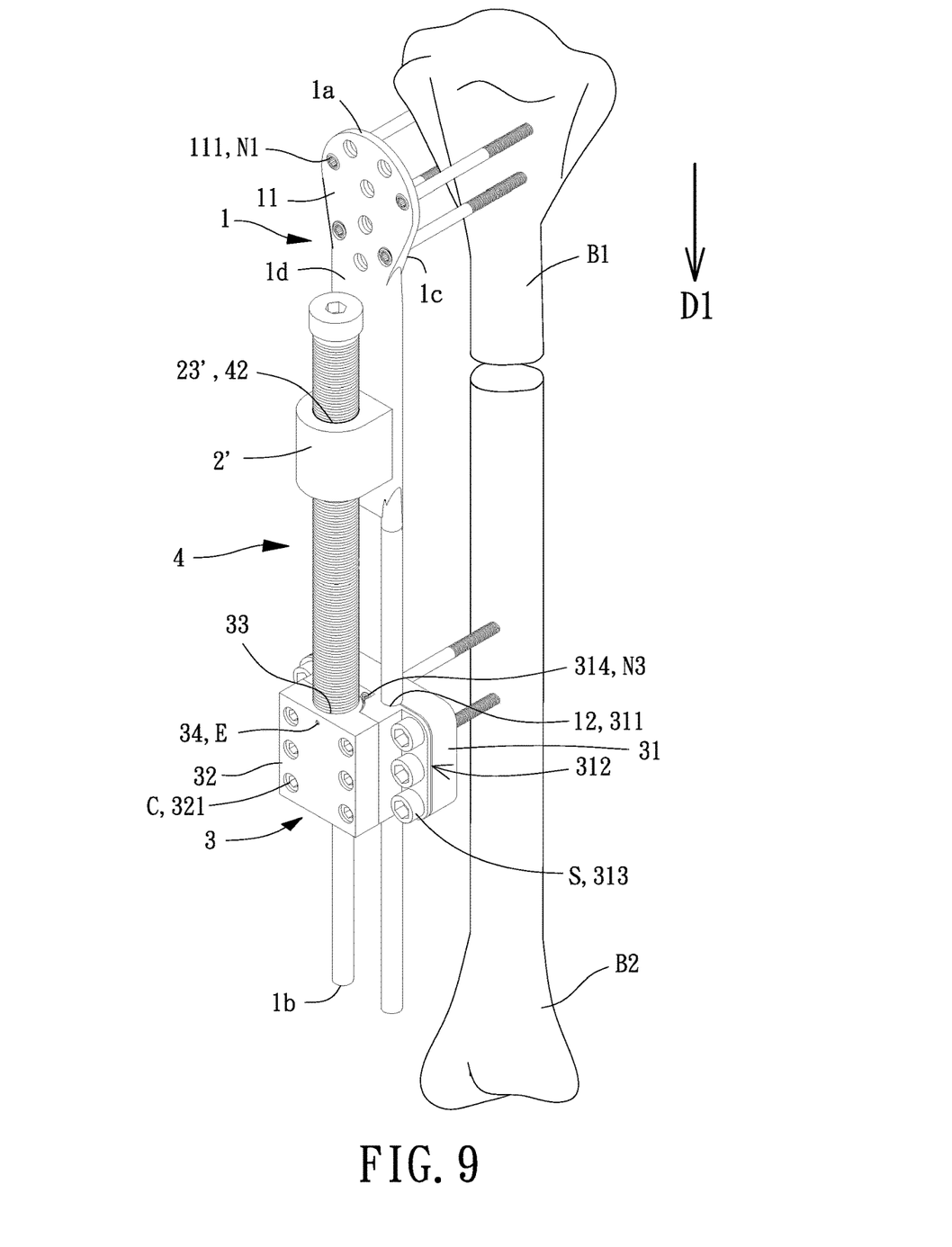
FIG. 9 is a perspective view of the adjustable external fixator according to the third embodiment of the present disclosure when utilized in bone lengthening.

With references to FIG. 9, the adjustable external fixator can also be utilized in bone lengthening. Since the positioning member 2' is integrally formed on the body 1, the surgeon needs not adjust the distance between the positioning member 2' and the fixation portion 11 of the body 1, improving convenience of the surgery.

According to the above, since the adjustable external fixator of the present disclosure has the body that can adhered on the patient's limb as well as the positioning member and the bone coupling member coupled with the body, the adjustable external fixator is provided with smaller volume and lighter weight, thus reducing the burden to the daily living of the patient.

Although the invention has been described in detail with reference to its presently preferable embodiments, it will be understood by one of ordinary skill in the art that various modifications can be made without departing from the spirit and the scope of the invention, as set forth in the appended claims.

What is claimed is:

1. An adjustable external fixator comprising:
   a body having opposite first and second ends and a first direction extending from the first end toward the second end, wherein the body comprises a fixation portion adjacent to the first end and away from the second end, and wherein the body further comprises a slideway extending in the first direction from the fixation portion;
   a positioning member arranged at the body, wherein the positioning member comprises a screw hole penetrating through the positioning member in the first direction;
   a bone coupling member arranged at the slideway of the body, wherein the bone coupling member comprises at least one bone coupling hole having an extending direction not parallel to the first direction, wherein the positioning member is located between the fixation portion of the body and the bone coupling member; and
   a threaded rod comprising a threaded section fastened with the screw hole of the positioning member, wherein an end of the threaded rod is adapted to abut against the bone coupling member, wherein at least one of the positioning member and the bone coupling member is slidably coupled to the slideway of the body, wherein the slideway is in a form of two elongated rods, wherein the bone coupling member comprises two apertures extending in the first direction through two opposite sides of the bone coupling member, wherein each of the two apertures comprises a through groove to form an adjustable slit, and wherein the two elongated rods of the body respectively extend in the two apertures.

2. The adjustable external fixator as claimed in claim 1, wherein the threaded rod further comprises a head and a terminal section, wherein the threaded section is located between the head and the terminal section, and wherein the bone coupling member comprises a blind hole aligned with the screw hole of the positioning member and adapted for receiving the terminal section of the threaded rod.

3. The adjustable external fixator as claimed in claim 2, wherein the bone coupling member further comprises a through hole communicating with the blind hole, wherein the through hole has an extending direction not parallel to an extending direction of the blind hole, wherein a circular groove is arranged at the terminal section of the threaded rod, wherein the circular groove communicates with the through hole when the terminal section of the threaded rod is received in the blind hole, and wherein the through hole is adapted for a securing component to extend therethrough into the circular groove.

4. The adjustable external fixator as claimed in claim 1, wherein the positioning member is integrally formed at the body.

5. The adjustable external fixator as claimed in claim 1, wherein the positioning member comprises at least one bone coupling hole having an extending direction not parallel to the first direction.

6. An adjustable external fixator comprising:
   a body having opposite first and second ends and a first direction extending from the first end toward the second end, wherein the body comprises a fixation portion adjacent to the first end and away from the second end, and wherein the body further comprises a slideway extending in the first direction from the fixation portion;
   a positioning member arranged at the body, wherein the positioning member comprises a screw hole penetrating through the positioning member in the first direction;
   a bone coupling member arranged at the slideway of the body, wherein the bone coupling member comprises at least one bone coupling hole having an extending direction not parallel to the first direction, wherein the positioning member is located between the fixation portion of the body and the bone coupling member; and a threaded rod comprising a threaded section fastened with the screw hole of the positioning member, wherein an end of the threaded rod is adapted to abut against the bone coupling member, wherein at least one of the positioning member and the bone coupling member is slidably coupled to the slideway of the body, wherein the slideway is in a form of two elongated rods, wherein the positioning member comprises two apertures extending in the first direction through two opposite sides of the positioning member, wherein each of the two apertures comprises a through groove to form an adjustable slit, and wherein the two elongated rods of the body respectively extend in the two apertures.

\* \* \* \* \*